March 2, 1976 L. H. SHOESMITH Plant Pat. 3,833
CHRYSANTHEMUM PLANT
(BRANDYWINE)
Filed Nov. 4, 1974
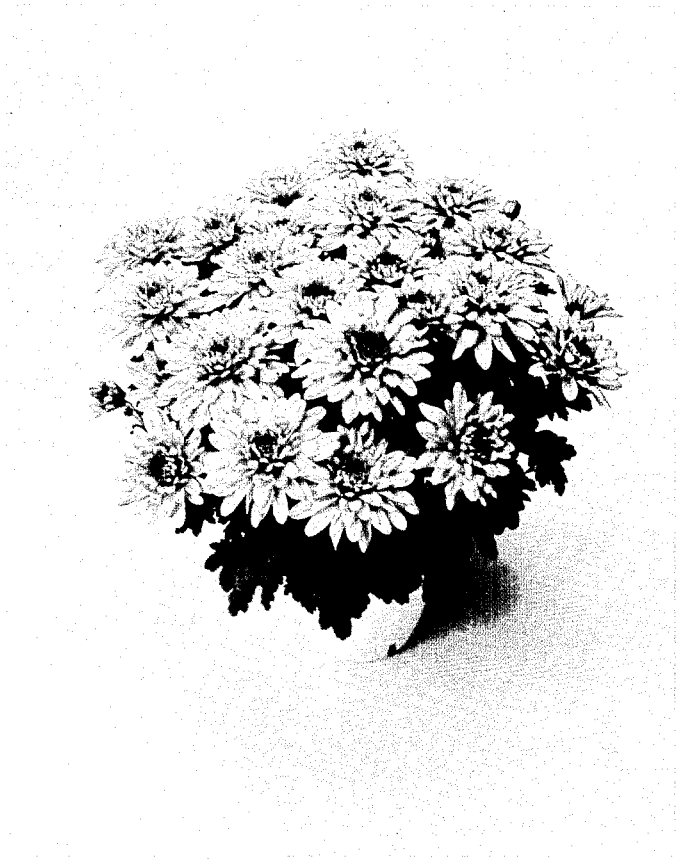
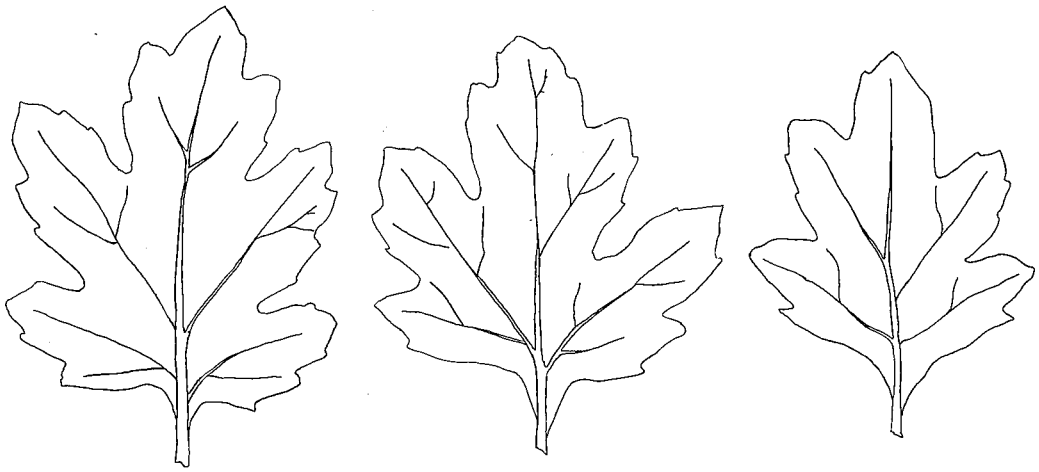

United States Patent

Plant Pat. 3,833

Patented Mar. 2, 1976

3,833

CHRYSANTHEMUM PLANT (BRANDYWINE)

Leonard H. Shoesmith, Westfield, Woking, Surrey, England, assignor to Pan-American Plant Company, West Chicago, Ill.

Filed Nov. 4, 1974, Ser. No. 520,429
Int. Cl. A01h 5/00
U.S. Cl. Plt—81 1 Claim

ABSTRACT OF THE DISCLOSURE

A new variety of chrysanthemum plant of the pot plant type characterized by the magenta rose coloring of its medium sized blooms which have a central cluster of dark colored florets surrounded by relatively large, outwardly spreading petals of a lighter pink color, its nine-week response as a disbudded plant, its ability to be flowered the year around with photoperiod control, and an excellent dispray pot habit.

BACKGROUND OF THE NEW PLANT

This new chrysanthemum plant was found by me, among a bench of seedling plants of the pot type and of unidentified parentage, at West Chicago, Ill., where breeding activities are carried on under my direction. Asexual propagation of this plant by means of cuttings has been carried on, under my direction at West Chicago, Ill., through many generations and its distinctive features have been found to be firmly fixed and to hold true. Propagation of this new variety is now being carried on, by means of vegetative cuttings, at West Chicago, Ill., and at Cortez, Fla.

DESCRIPTION OF THE DRAWINGS

This new variety of chrysanthemum plant is illustrated by the accompanying photographic drawing which shows a typical plant in full bloom and the color and flower form of its blossoms, the colors being reproduced as nearly true as reasonably possible by conventional photographic procedures. The drawing also shows, by pen and ink drawings, the distinctive configuration of the leaves of the new plant, the specimens being taken at several stages of maturity from a blooming plant.

DESCRIPTION OF THE NEW PLANT

The following is a detailed description of this new variety of chrysanthemum plant with color designations according to the Horticultural Colour Chart (HCC) by Robert F. Wilson, published by The Royal Horticultural Society of London, England.

The plant

Origin: Seedling.
Parentage: Unidentified. Seedling found among random pollinated greenhouse plants.
Classification:
*Botanic.*—*Chrysanthemum morifolium.*
*Commercial.*—Greenhouse pot plant.
Form: Perennial herbaceous bush.
Height: 10 to 15 inches.
Growth: Upright and spreading.
Branching: Numerous lateral breaks with thin but strong stems.
Foliage: Quantity—moderate.
*Leaf size.*—3¼ to 4 inches long x 2¾ to 3 inches wide.

*Shape.*—Ovate to obovate and deeply lobed with one mucronate tip on each lobe.
*Surface texture.*—Puberulous.
*Venation.*—Pinnately veined.
*Color.*—Upper side—Spinach Green 0960. Under side—Spinach Green 0960/2.
*Petioles.*—About ¾ inch long.

The bud

Form: Gloublar.
Size: About ⅜ inch in diameter and 5/16 inch in depth when phyllaries first open.
Color:
*When phyllaries first divide.*—Primrose Yellow 601/3.
*When florets begin to unfurl.*—Erythrite Red 0027/1.
Phyllaries: The outside of the receptacle bears many involucral, upstanding, spear-shaped bracts.
*Color.*—Inside—Spinach Green 0960/1. Outside—Spinach Green 0960/1.
*Surface texture.*—Pubescent.
Peduncle: Erect—about 1 inch long.
*Surface texture.*—Pubescent.

The flower

Flowering ability: Plant can be flowered the year around with photoperiod control.
*Response.*—9 week.
*Recommended flowering.*—North—April through November. South—Year around.
*Natural season flowering.*—About October 27 to November 5.
Blooms:
*Flower type.*—Decorative.
*Borne.*—Either singly when disbudded or in multiples of 6 or more when grown as a spray plant.
*Size.*—Medium. Diameter—3 to 3¼ inches. Depth—¾ inch.
*Shape.*—Cup-shaped, when bloom first opens, becoming more flat as bloom matures.
*Florets.*—Many in number. Composite with generally upstanding inner petals and many spreading outer ray-like petals having very slight reflexing and no longitudinal petal roll.
*Color.*—Outer florets—Magenta Rose 027/2 to 027/3. Intermediate florets—Magenta Rose 027/1. Inside florets—Magenta Rose 027. Reverse side—Outer, short—Magenta Rose 027/3. Reverse of inside floret—Magenta Rost 027/2. The colors tend to be lighter when bloomed during periods of high light intensity.
*Firmness.*—Medium.
*Appearance.*—Satiny.
Peduncle: Upright—1¾ to 2 inches long.
*Color.*—Spinach Green 0960/2.
Discoloration: Some fading to lighter in high light intensity.
Fragrance: None.
Persistence: Florets hang on and dry.
Lasting quality: 3 weeks on plant. Not recommended as a cut flower.

Reproductive organs

Stamens: 5 syngenesious stamens, connate by their anthers to form a cylinder about the style.

*Filaments.*—1/16 inch long. Light yellow in color.

*Pollen.*—Color—Yellow.

Pistils: Number—one to each ray floret.

*Style.*—1/4 inch long.

*Stigma.*—Color—Barium Yellow 503.

Ovaries: Inferior bicarpellate.

This new variety of chrysanthemum plant is particularly characterized by the dark and light pink color combination of its three and three and one-half inch diameter decorative form of flower. This plant produces 5 or 6 lateral breaks when pinched, its vigor and plant habit are similar to the cultivar Hostess (Plant Pat. 3,224), and it performs as described when flowered as a disbud or spray pot plant from Easter to Thanksgiving at latitude of 42° North.

I claim:

1. A new and distinctive variety of chrysanthemum plant, substantially as herein shown and described, characterized by the dark pink center and light pink outer petal coloring of its decorative type flowers, its production of five to six lateral breaks when pinched, and its excellent dispray pot habit.

No references cited.

ROBERT E. BAGWILL, Primary Examiner